United States Patent
Savord et al.

(10) Patent No.: US 6,685,647 B2
(45) Date of Patent: Feb. 3, 2004

(54) ACOUSTIC IMAGING SYSTEMS ADAPTABLE FOR USE WITH LOW DRIVE VOLTAGES

(75) Inventors: Bernard J. Savord, Andover, MA (US); William J. Ossmann, Acton, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 30 days.

(21) Appl. No.: 09/894,709

(22) Filed: Jun. 28, 2001

(65) Prior Publication Data

US 2003/0013967 A1 Jan. 16, 2003

(51) Int. Cl.[7] .................................................. A61B 8/14
(52) U.S. Cl. ..................................................... 600/459
(58) Field of Search ................................ 600/407–471; 601/2, 3; 310/317–334; 367/7, 11, 130, 138; 73/597, 598, 625, 626; 29/25.35; 128/916

(56) References Cited

U.S. PATENT DOCUMENTS

| 4,296,349 A | | 10/1981 | Nakanishi et al. ........... 310/335 |
|---|---|---|---|
| 4,915,115 A | | 4/1990 | Sasaki et al. ........... 128/660.05 |
| 5,311,095 A | * | 5/1994 | Smith et al. ................ 310/334 |
| 5,608,692 A | * | 3/1997 | Toda .......................... 310/325 |
| 6,045,506 A | * | 4/2000 | Hossack ..................... 600/443 |
| 6,049,159 A | | 4/2000 | Barthe et al. ............... 310/334 |
| 6,497,665 B1 | * | 12/2002 | Hunt et al. ................. 600/458 |
| 6,508,775 B2 | * | 1/2003 | McKenzie et al. ............. 601/2 |

* cited by examiner

Primary Examiner—Ali M. Imam
(74) Attorney, Agent, or Firm—John Vodopia (57) ABSTRACT

Acoustic imaging systems are provided. A representative acoustic imaging system includes a transducer that incorporates a backing and an acoustic element extending from the backing. The acoustic element includes a piezoelectric element and a de-matching layer. The de-matching layer is arranged between the backing and the piezoelectric element and exhibits an acoustic impedance greater than that of the piezoelectric element. The piezoelectric element exhibits a thickness that is less than one-half of a wavelength to be generated by the piezoelectric element. Methods also are provided.

23 Claims, 6 Drawing Sheets

ACOUSTIC IMAGING SYSTEMS ADAPTABLE FOR USE WITH LOW DRIVE VOLTAGES

BACKGROUND OF THE INVENTION

1. Field of the Invention

The present invention generally relates to acoustic imaging. More specifically, the invention relates to systems and methods utilizing transducers that are adapted to operate with low drive voltages.

2. Description of the Related Art

A prior art two-dimensional ("2-D") ultrasound transducer typically includes a linear array of transducer elements that are capable of acquiring two-dimensional image data. For example, a 2-D transducer can include a linear array of one hundred and twenty eight (128) elements. In contrast, a three-dimensional ("3D") transducer is capable of acquiring three-dimensional image data. This is accomplished by providing the elements of such a 3-D transducer in a two-dimensional array. Such an array may include over 1,000 elements, for example.

Figure 1:
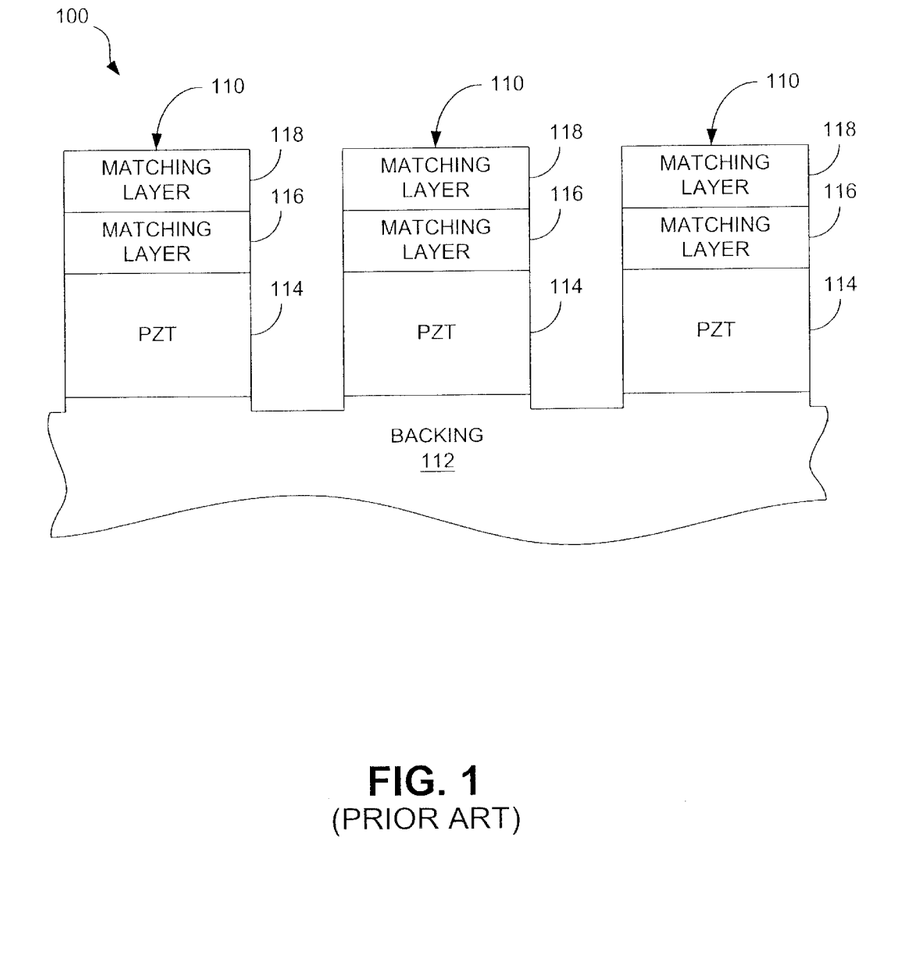
FIG. 1 is a schematic diagram depicting a representative portion of a prior art transducer.

A representative example of a portion of a conventional transducer is depicted schematically in FIG. 1. Transducer 100 of FIG. 1 includes an array of transducer elements 110 that are mounted to a backing 112. Each element 110 incorporates a piezoelectric element 114, such as a lead zirconate titanate piezoelectric element ("PZT"), that is adapted to generate an acoustic wave in response to an applied electric field. Such an electric field is applied to the PZT by selectively applying a voltage to electrode layers (not shown) that are formed on opposing sides of the PZT. Each element 110 also includes one or more acoustic matching layers, e.g., layers 116 and 118. Each of the acoustic matching layers exhibits an acoustic impedance that is less than the acoustic impedance of the PZT, but greater than the acoustic impedance of the body into which acoustic waves are to be propagated. This arrangement couples acoustic energy more efficiently between the element and the body.

Prior art transducers, such as transducer 100 of FIG. 1, typically operate at one-half wave resonance. That is, the PZT of each element exhibits a thickness that corresponds to one-half of a wavelength to be generated by the PZT. This thickness typically necessitates the use of high drive voltages, e.g., 170V, for achieving the desired acoustic pressures. More specifically, the PZT changes shape in response to the applied electric field, therefore, the thicker the PZT, the higher the applied voltage required to achieve the same electric field across the PZT.

Figure 2:
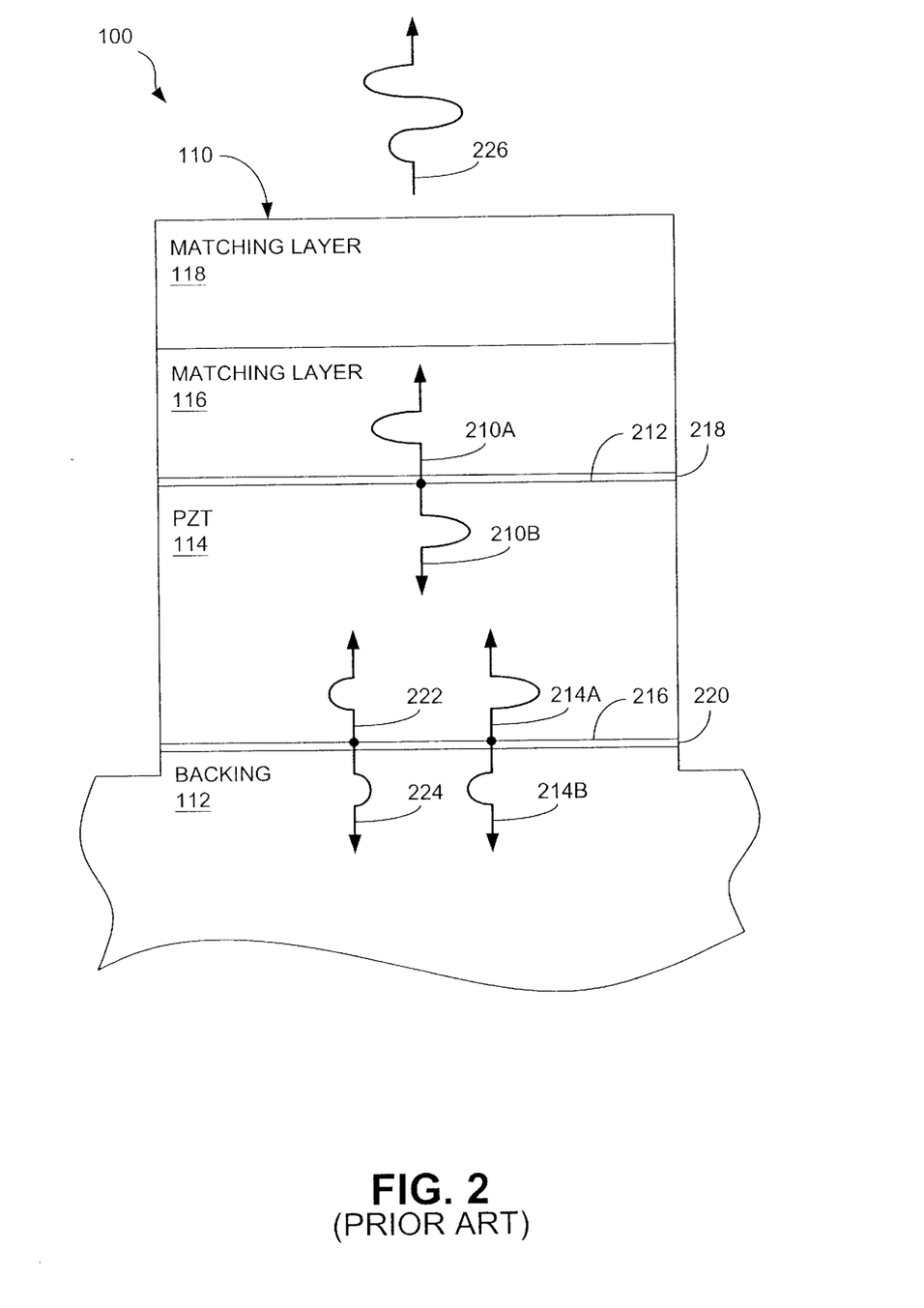
FIG. 2 is a schematic diagram depicting a transducer element of FIG. 1 showing detail of propagation of an acoustic wave.

Referring now to FIG. 2, operation of transducer element 110 will be described in greater detail. As shown in FIG. 2, PZT 114 produces three forward-directed waves. More specifically, PZT 114 generates a first pair of waves, i.e., a forward-directed wave 210A and a corresponding backward-directed wave 210B, at the front surface 212 of the PZT. A second pair of waves, i.e., a forward-directed wave 214A and a corresponding backward-directed wave 214B, is generated at the back surface 216 of the PZT. Waves 210A, 210B and 214A, 214B are generated when an electric field is applied to the PZT via electrodes 218 and 220. Thereafter, wave 210B yields a reflected (forward-directed) wave 222 and an absorbed wave 224. Wave 224 is absorbed by backing 112, which exhibits an acoustic impedance less than that of the PZT. Forward-directed waves 210A, 214A and 222 then interfere with each other to produce a resultant wave 226.

One of the difficulties in providing an acoustic imaging system that utilizes a 3-D transducer is associated with integrating electronic components of the transducer within the housing of the transducer. In particular, the housing of a 2-D transducer may only include 128 elements, whereas the housing of a 3-D transducer may include over 1000 elements. Thus, the increased number of elements can hinder component integration.

Operational characteristics of conventional transducer elements also can render these elements less than desirable for use in a 3-D transducer. For instance, conventional transducer elements typically operate with high drive voltages (described hereinbefore), which tend to be incompatible for use with integrated circuitry. Therefore, when using conventional transducer elements in a 3-D transducer, a desired level of component integration may not be achievable through the use of integrated circuitry. Thus, it can be appreciated that there is a need for improved systems and methods that address the aforementioned and/or other shortcomings of the prior art.

SUMMARY OF THE INVENTION

Briefly described, the present invention relates to acoustic imaging. In this regard, embodiments of the invention may be construed as acoustic imaging systems. A representative acoustic imaging system includes a transducer that incorporates a backing and an acoustic element extending from the backing. The acoustic element includes a piezoelectric element and a de-matching layer. The de-matching layer is arranged between the backing and the piezoelectric element and exhibits an acoustic impedance greater than that of the piezoelectric element. Additionally, the piezoelectric element exhibits a thickness that is less than one-half of a wavelength to be generated by the piezoelectric element.

Other embodiments of the invention can be construed as methods for acoustically imaging a body. In this regard, a representative method includes: providing a transducer having a backing and an acoustic element extending from the backing; generating acoustic waves with the acoustic element; and substantially preventing acoustic energy generated by the acoustic element from propagating into the backing of the transducer.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 3:
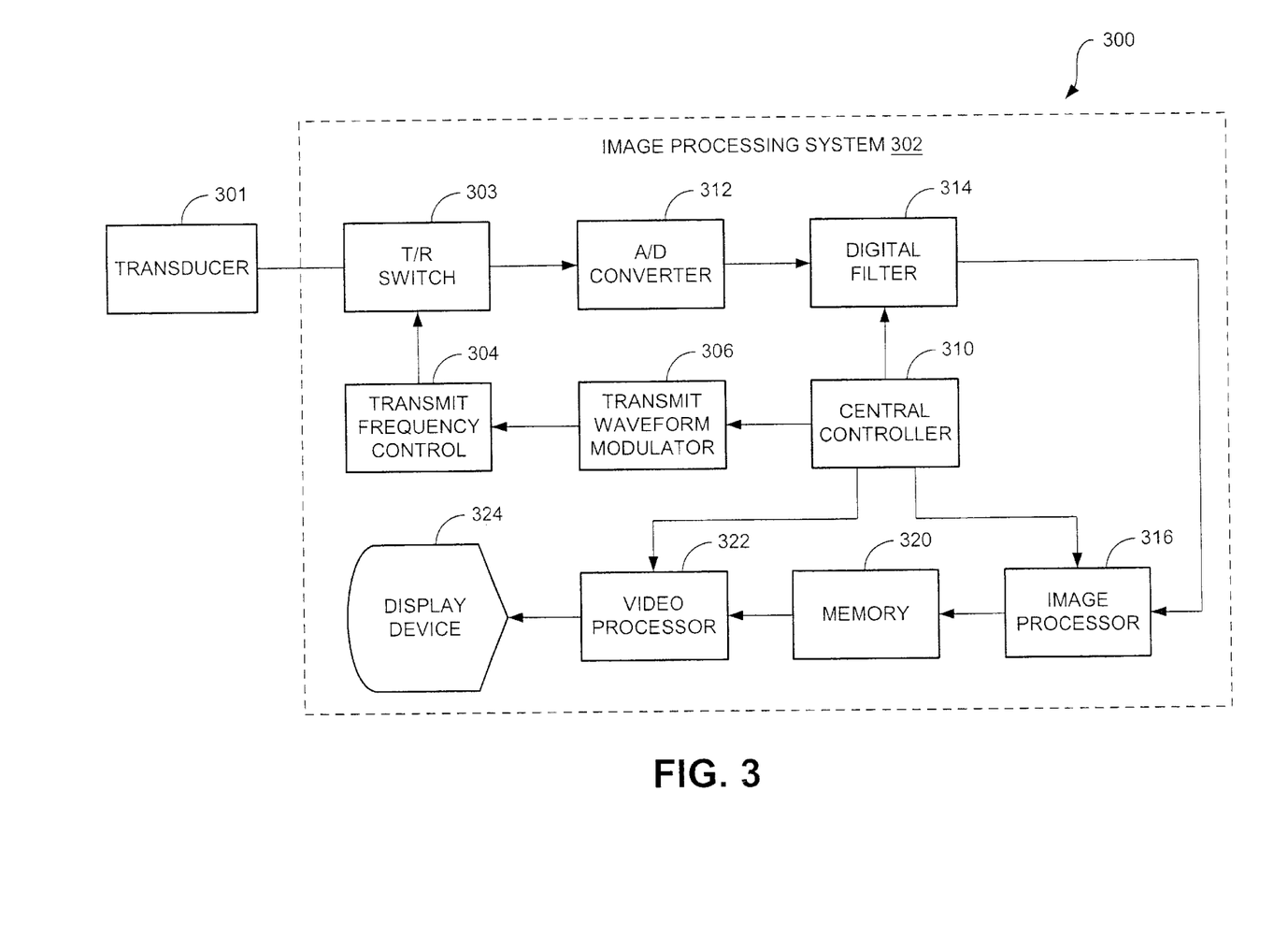
FIG. 3 is a schematic diagram depicting a representative embodiment of an acoustic imaging system of the present invention.

Reference will now be made to the drawings wherein like reference numerals indicate corresponding parts throughout the several views. In this regard, FIG. 3 depicts a representative embodiment of an acoustic imaging system 300 of the present invention. As described in greater detail hereinafter, acoustic imaging system 300 includes a transducer 301 that is adapted to operate using a relatively low drive voltage while facilitating acquisition of 3-D image data. It should be appreciated that FIG. 3 does not necessarily illustrate every component of the representative embodiment of the acoustic imaging system, emphasis instead being placed upon the components most relevant to the systems and/or methods disclosed herein.

As depicted in FIG. 3, imaging system 300 includes an image processing system 302 that electrically communicates with transducer 301. In particular, transducer 301 is electrically connected to a T/R switch 303 of image processing system 302. T/R switch 303 places the transducer in either a transmit or receive mode. In order to facilitate transmission of acoustic energy via the transducer during operation in the transmit mode, image processing system 302 includes a transmit frequency controller 304 that sets the transmit frequency of transmit signals and a transmit waveform modulator 306 that modulates the various transmitted signal lines. The transmit frequency controller 304 and transmit waveform modulator 306 typically operate under control of a central controller 310.

In order to facilitate reception of acoustic energy via the transducer during operation in the receive mode, image processing system 302 includes an A/D converter 312, which converts analog signals received from transducer 301 into digital signals. A digital filter 314, e.g., an RF filter, filters signals outside a desired receive band from the received data. An image processor 316 is provided for processing received data, with processed data then typically being provided to memory 320 for storage, as required. A video processor 322 also preferably is provided for enabling display of information corresponding to the received data on a display device 324.

As mentioned hereinbefore, transducers of the present invention are adapted to operate using lower voltages than those used in typical prior art transducers, such as transducer 100 depicted in FIGS. 1 and 2, while providing the desired acoustic pressures. By way of example, some embodiments of the invention can be configured to generate an acoustic wave exhibiting a mechanical index of approximately 1.9 in response to receiving a drive voltage of less than approximately 90 volts for a 2 MHz transducer. Other embodiments can be configured to generate an acoustic wave exhibiting a mechanical index of approximately 1.9 in response to receiving a drive voltage of less than approximately 50 volts for a 5 MHz transducer. It should be noted that embodiments of the invention can be configured to generate acoustic pressures, use drive voltages and/or exhibit mechanical indices other than those expressly recited herein.

In order to achieve this characteristic, transducers of the invention incorporate piezoelectric elements that are thinner than piezoelectric elements typically used in transducers of the prior art. By using thinner piezoelectric elements, a lower voltage can be used for generating the same amount of acoustic energy per element. This is because the acoustic energy generated by a transducer element is directly proportional to the electrical field applied to the piezoelectric element of the transducer element. A representative embodiment of a transducer of the invention is depicted in FIG. 4.

Figure 4:
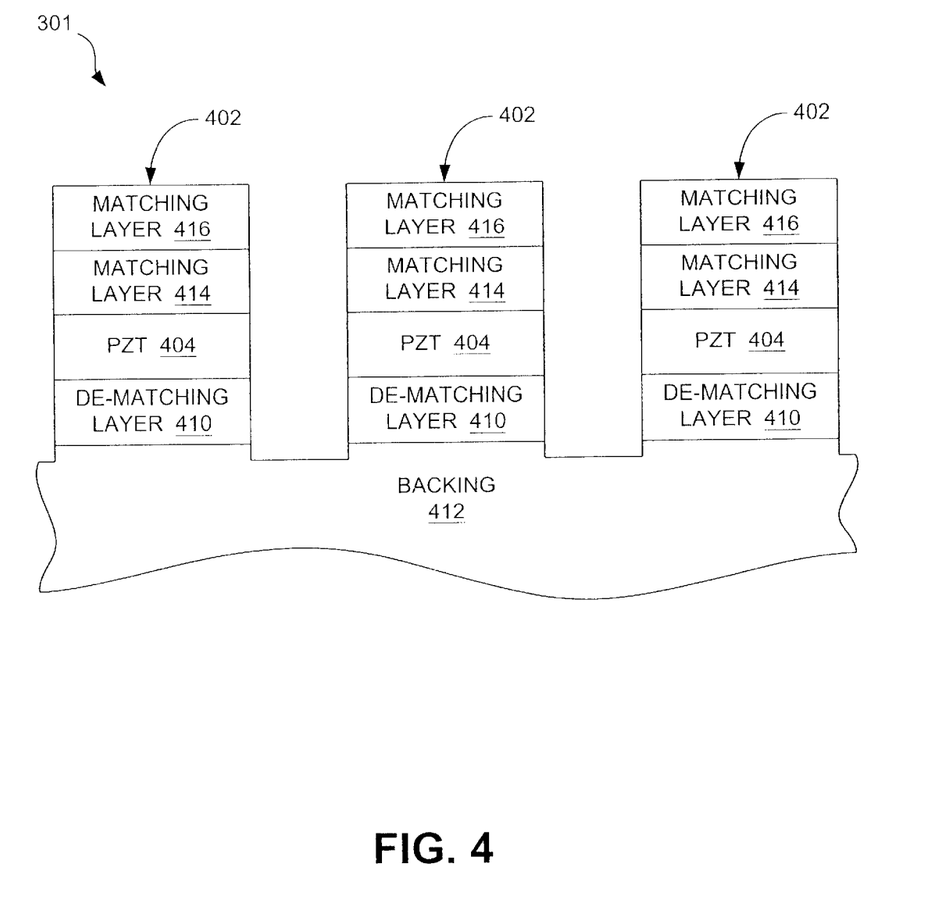
FIG. 4 is a schematic diagram depicting a representative portion of an embodiment of the transducer of the present invention.

As shown in FIG. 4, transducer 301 includes multiple transducer elements 402 that are arranged in an array. In embodiments configured for acquiring 3-D image data, the transducer elements are arranged in a two-dimensional array. Each element 402 includes a piezoelectric element 404, such as a lead zirconate titanate piezoelectric element ("PZT"), although other materials can be used. For ease of description, and not for the purpose of limitation, piezoelectric element 404 may be referred to herein as "PZT."

Figure 5:
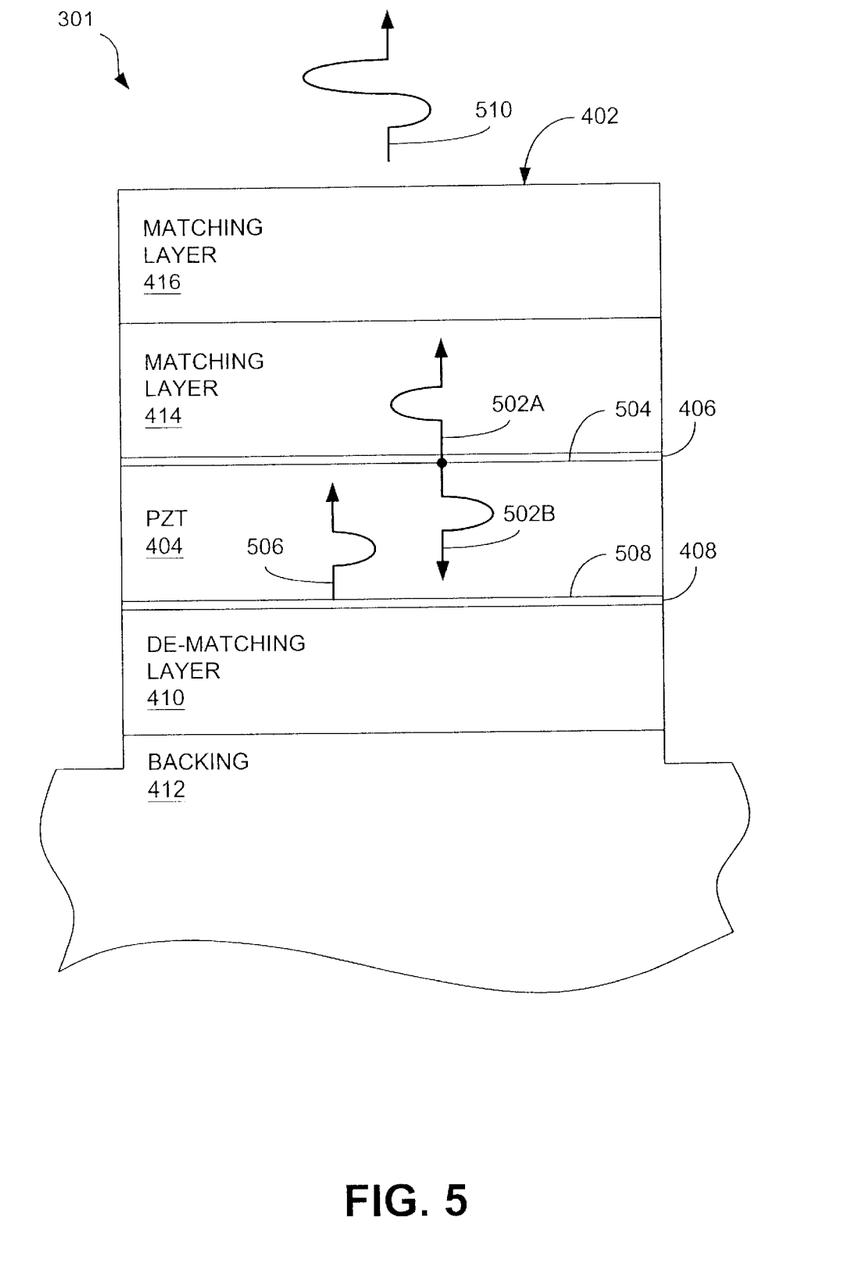
FIG. 5 is a schematic diagram depicting an element of the transducer of FIG. 4 showing detail of propagation of an acoustic wave.

Each PZT is engaged between electrodes 406 and 408 (depicted in FIG. 5). The electrodes are configured to apply an electric field across the PZT to cause a change in shape of the PZT. Attached to electrode 408 is an acoustic de-matching layer 410. The de-matching layer preferably exhibits an acoustic impedance that is greater than the acoustic impedance of the PZT. For example, the PZT can have an acoustic impedance of approximately 30 Mrayls and the de-matching layer can have an acoustic impedance of approximately 100 Mrayls. Such an impedance mismatch substantially prevents acoustic energy from propagating into backing 412, which is attached to de-matching layer 410. Thus, the de-matching layer functions as means for substantially preventing acoustic energy generated by a corresponding acoustic element from propagating into the backing. In some embodiment, more than one de-matching layer can be used.

Backing 412 preferably exhibits an acoustic impedance that is less than the acoustic impedance of the PZT. For example, the backing can have an acoustic impedance of approximately 6 MRayls. The impedance mismatch between the de-matching layer and the backing also prevents sound from being propagated into the backing. Based on the aforementioned acoustic impedances, i.e., a PZT of approximately 30 Mrayls, a de-matching layer of approximately 100 Mrayls having a thickness of approximately one-quarter wavelength, and a backing of approximately 6 Mrayls, the PZT experiences an effective acoustic of approximately 1666 Mrayls. Clearly, the acoustic impedance of the backing, de-matching layer and/or PZT can be selected based upon the particular application.

Additionally, one or more acoustic matching layers, such as matching layers 414 and 416, are arranged at the distal end of each element. The matching layers exhibit an acoustic impedance that is less than that of the corresponding PZT, but greater than the acoustic impedance of the body into which acoustic waves are to be propagated. Thus, the matching layer(s) function as means for reducing acoustic reflections at the interface formed between the element and the body.

As mentioned hereinbefore, each PZT 404 preferably exhibits a thickness that is less than one-half of the wavelength of acoustic energy to be propagated. In some embodiments, PZT thickness is approximately one-quarter wavelength or less. As described in greater detail hereinafter, by using PZT's that are less than one-half wavelength in thickness, transducers of the invention can operate with relatively low drive voltages. This enables the transducers to use high density integrated circuitry, e.g., integrated circuitry with a 3.5 micron gate length, thereby facilitating integration of components within the housing of the transducer. In this manner, a significant improvement in component integration can be achieved.

Operation of a representative transducer 301 will now be described in relation to FIG. 5. In FIG. 5, PZT 404 produces two forward-directed waves. More specifically, PZT 404 generates a first pair of waves, i.e., a forward-directed wave 502A and a backward-directed wave 502B, at the front surface 504 of the PZT. Waves 502A and 502B are generated when an electric field is applied across the PZT by electrodes 406 and 408. A reflected (forward-directed) wave 506 corresponding to backward-directed wave 502B also is formed at the interface between the back surface 508 of the PZT and the de-matching layer. Forward-directed waves 502A and 506 then interfere with each other to produce a resultant wave 510. In particular, the resultant wave 510 tends to exhibit a higher amplitude waveform than a corresponding waveform generated by a typical prior art transducer when an equivalent drive voltage is applied (See wave 226 of FIG. 2, for example). This is due, at least in part, to the impedance mismatch between the de-matching layer 410 and the PZT 404 that substantially prevents acoustic energy from propagating into backing 412. Since less energy is lost to the backing, more energy can be directed toward the body to be imaged.

Additionally, the reduced thickness of the PZT tends to produce a higher amplitude waveform compared to a corresponding waveform generated by a typical prior art transducer at an equivalent drive voltage. This is due, at least in part, to the reduced thickness of the PZT enabling an electric field to be applied to the PZT with a lower voltage than that required to apply a similar electric field across a thicker PZT. Moreover, since the PZT is less than one-half wavelength in thickness, the propagation delay between waves 506 and 502A is less than that of the forward-directed waves generated by a typical prior art transducer (See FIG. 2). Therefore, the waves interfere with each other more constructively. This also tends to produce a resultant wave that exhibits a shorter pulse width than the resultant wave generated by a one-half wavelength PZT.

Since acoustic energy typically is not propagated to backing 412, various components can be arranged within and/or behind the backing. For example, mechanical fasteners and/or electrical contacts can be provided within and/or behind the backing. In contrast, if acoustic energy were to propagate into the backing, such as is known in the prior art, such components could produce acoustic artifacts by reflecting some of the acoustic energy. These artifacts tend to degrade the performance of a transducer.

Figure 6:
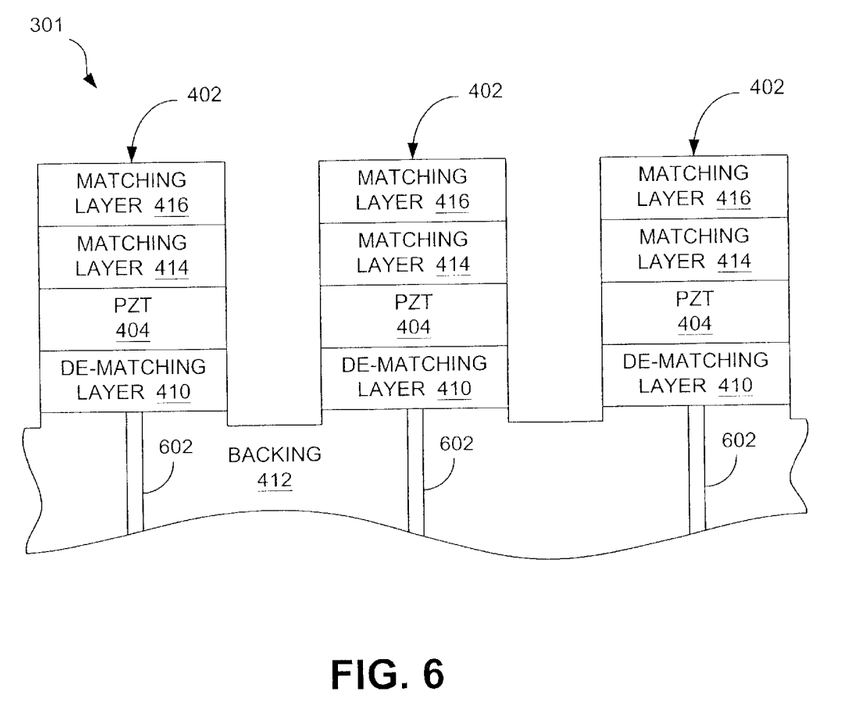
FIG. 6 is a schematic diagram depicting a representative portion of an alternative embodiment of the transducer of the present invention.

A representative embodiment of a transducer of the invention that incorporates components arranged within the backing is depicted in FIG. 6. In FIG. 6, electrical traces 602 extend through at least a portion of backing 412 and terminate by electrically engaging a corresponding de-matching layer 410 of an element 402. Preferably, each de-matching layer is formed of a conductive material. In these embodiments, the de-matching layer can be used as an electrical connection for transmitting signals between PZT's 404 and/or associated electrodes and components engaging the traces, i.e., components (not shown) that are arranged within and/or behind the backing. Thus, the trace(s) and/or de-matching layer(s) function as means for propagating electrical signals to and/or from the PZT(s) and/or electrode(s).

The foregoing description has been presented for purposes of illustration and description. It is not intended to be exhaustive or to limit the invention to the precise forms disclosed. Modifications or variations are possible in light of the above teachings. The embodiment or embodiments discussed, however, were chosen and described to provide the best illustration of the principles of the invention and its practical application to thereby enable one of ordinary skill in the art to utilize the invention in various embodiments and with various modifications as are suited to the particular use contemplated. All such modifications and variations, are within the scope of the invention as determined by the appended claims when interpreted in accordance with the breadth to which they are fairly and legally entitled.

What is claimed is:

1. An acoustic imaging system comprising:

a transducer having a backing and an acoustic element, said acoustic element extending from said backing, said acoustic element including a piezoelectric element and a de-matching layer, said de-matching layer being arranged between said backing and said piezoelectric element, said piezoelectric element exhibiting a thickness less than one-half of a wavelength to be generated by said piezoelectric element, said de-matching layer exhibiting an acoustic impedance greater than an acoustic impedance of said piezoelectric element, said acoustic element is configured to generate an acoustic wave exhibiting a mechanical index of approximately 1.9 in response to receiving a drive voltage of less than 90 volts.

2. The acoustic imaging system of claim 1, wherein said piezoelectric element exhibits a thickness equal to approximately one-quarter of a wavelength to be generated by said piezoelectric element.

3. The acoustic imaging system of claim 1, wherein said piezoelectric element exhibits a thickness of less than one-quarter of a wavelength to be generated by said piezoelectric element.

4. The acoustic imaging system of claim 1, wherein said backing exhibits an acoustic impedance less than said acoustic impedance of said piezoelectric element.

5. The acoustic imaging system of claim 1, wherein said backing exhibits an acoustic impedance less than said acoustic impedance of said de-matching layer.

6. The acoustic imaging system of claim 1, wherein said transducer is a 2 MHz transducer.

7. The acoustic imaging system of claim 1, wherein said transducer is a 5 MHz transducer.

8. The acoustic imaging system of claim 1, wherein said transducer is configured for acoustically imaging a body, and further comprising:

means for reducing acoustic reflections at an interface between said transducer and the body.

9. The acoustic imaging system of claim 1, wherein said transducer is configured for acoustically imaging a body, and further comprising:

a matching layer engaging said piezoelectric element, said piezoelectric element being arranged between said matching layer and said de-matching layer, said matching layer exhibiting an acoustic impedance less than said acoustic impedance of said piezoelectric element such that said matching layer reduces acoustic reflections at an interface between said transducer and the body.

10. The acoustic imaging system of claim 1, wherein said de-matching layer is formed, at least in part, of an electrically conductive material, and further comprising:

an electrical trace extending at least partially through said backing, said electrical trace electrically engaging said de-matching layer such that signals can be propagated between said electrical trace and said piezoelectric element via said de-matching layer.

11. The acoustic imaging system of claim 1, further comprising:
a second acoustic element extending from said backing; and
a third acoustic element extending from said backing, said first acoustic element, said second acoustic element, and said third acoustic element forming a two-dimensional array of acoustic elements.

12. The acoustic imaging system of claim 1, further comprising:
an image processing system electrically communicating with said transducer, said image processing system being adapted to transmit electrical signals to said transducer such that said acoustic element generates an acoustic wave, and receive electrical signals from said transducer.

13. The acoustic imaging system of claim 1, wherein said backing has an acoustic impedance greater than 1 MRayls.

14. A method for acoustically imaging a body, said method comprising:
providing a transducer having a backing and an acoustic element extending from the backing, said acoustic element including a piezoelectric element and a de-matching layer, said de-matching layer being arranged between said backing and said piezoelectric element;
generating acoustic waves with the acoustic element, said acoustic element is configured to generate acoustic waves exhibiting a mechanical index of approximately 1.9 in response to receiving a drive voltage of less than 90 volts; and
substantially preventing acoustic energy generated by the acoustic element from propagating into the backing of the transducer.

15. The method of claim 14, wherein said piezoelectric element exhibiting a thickness equal to approximately one-quarter of a wavelength to be generated by the piezoelectric element.

16. The method of claim 14, wherein the said piezoelectric element exhibiting a thickness of less than one-quarter of a wavelength to be generated by the piezoelectric element.

17. The method of claim 14, wherein substantially preventing acoustic energy generated by the acoustic element from propagating into the backing of the transducer comprises:
providing the de-matching layer exhibiting an acoustic impedance greater than an acoustic impedance of the piezoelectric element.

18. The method of claim 17, wherein the de-matching layer is electrically conductive, and further comprising:
propagating electrical signals to the piezoelectric element via the de-matching layer.

19. The method of claim 17, wherein the de-matching layer is electrically conductive, and further comprising:
propagating electrical signals from the piezoelectric element via the de-matching layer.

20. The method of claim 14, wherein said backing has an acoustic impedance greater than 1 MRayls.

21. An acoustic imaging system comprising:
a transducer including:
a backing; and
an array of acoustic elements extending from said backing, at least one of said acoustics elements including a piezoelectric element exhibiting a thickness less than one-half of a wavelength to be generated by said piezoelectric element, and means for substantially preventing acoustic energy generated by said acoustic element from propagating into said backing, said transducer is configured to generate acoustic waves exhibiting a mechanical index of approximately 1.9 in response to receiving a drive voltage of less than 90 volts.

22. The acoustic imaging system of claim 21, wherein said means for substantially preventing acoustic energy from propagating into said backing comprises:
means for propagating electrical signals to the piezoelectric element.

23. The acoustic imaging system of claim 21, wherein said backing has an acoustic impedance greater than 1 MRayls.

* * * * *